(12) United States Patent
Pell et al.

(10) Patent No.: US 10,729,648 B2
(45) Date of Patent: Aug. 4, 2020

(54) METHOD OF DELIVERING ALCOHOL

(71) Applicant: BN INTELLECTUAL PROPERTIES, INC., St. Petersburg, FL (US)

(72) Inventors: Donald M. Pell, St. Petersburg, FL (US); Frank Caiazzo, Brooksville, FL (US); Paula Pell, St. Petersburg, FL (US); Govindan P. Nair, Seminole, FL (US); Michael P. Spuza, Largo, FL (US); Nicholas A. Havercroft, Scunthorpe (GB)

(73) Assignee: BN INTELLECTUAL PROPERTIES, INC., St. Petersburg, FL (US)

( * ) Notice: Subject to any disclaimer, the term of this patent is extended or adjusted under 35 U.S.C. 154(b) by 0 days.

(21) Appl. No.: 16/230,992

(22) Filed: Dec. 21, 2018

(65) Prior Publication Data

US 2020/0197299 A1 Jun. 25, 2020

(51) Int. Cl.
*A61K 9/00* (2006.01)
*A61K 31/045* (2006.01)
*A61P 25/32* (2006.01)

(52) U.S. Cl.
CPC .......... *A61K 9/0078* (2013.01); *A61K 31/045* (2013.01); *A61P 25/32* (2018.01)

(58) Field of Classification Search
None
See application file for complete search history.

(56) References Cited

U.S. PATENT DOCUMENTS

2004/0256745 A1* 12/2004 Simler ................ A61K 31/045
261/121.1
2017/0348494 A1* 12/2017 Havercroft ........ A61M 15/0021

OTHER PUBLICATIONS

A. Ari. Jet, Ultrasonic, and Mesh Nebulizers: An Evaluation of Nebulizers for Better Clinical Outcomes. Eurasian Journal of Pulmonology 2014; 16: 1-7. (Year: 2014).*

* cited by examiner

*Primary Examiner* — Michael P Cohen
(74) *Attorney, Agent, or Firm* — Hauptman Ham, LLP

(57) ABSTRACT

An active mesh nebulizer is used to generate a distribution of liquid particles or droplets having a diameter ranging from about 0.5 to about 5 micrometers ($\mu$m). Delivery and ingestion, by inhalation, of ethyl alcohol solution particles leads to rapid uptake of the alcohol solution by brain tissue, and avoids damage to the liver, gastrointestinal tract, and/or peripheral nervous system consistent with drinking ethyl alcohol. A brain effect of ethyl alcohol absorbed through alveoli in the lung occurs within less than 60 seconds, and body effects of alcohol consumption are reduced or eliminated. Delivery of ethyl alcohol to a user by absorption through alveoli provides a user with a brain effect while allowing tissue damage from drinking alcohol to heal. A lock out barcoded capsule containing ethyl alcohol, tethered to a smartphone application, prevents unauthorized use by non-designated users, or abuse by a designated user.

13 Claims, 1 Drawing Sheet

100

105 Determine whether an operation limit is exceeded — Yes → 140 End nebulizer operation No ↓

110 Position an active mesh of a nebulizer in contact with an ethyl alcohol solution.

115 Active the active mesh to perform a cleaning operation.

120 Determine whether inhalation is occurring → 122 Wait

Yes ↓

125 Activate the active mesh to perform a volatilization operation.

130 During the volatilization operation, direct a stream of solution particles into a flow of air for respiration.

135 Terminate the volatilization process

FIG. 1

METHOD OF DELIVERING ALCOHOL

PRIORITY CLAIM AND CROSS-REFERENCE

The contents of U.S. patent application Ser. No. 16/025,437 entitled MODIFIED NEBULIZER, METHOD AND SYSTEM FOR DELIVERING PHARMACEUTICAL PRODUCTS TO AN INDIVIDUAL, and filed on Jul. 2, 2018, are incorporated herein by reference. The contents of U.S. patent application Ser. No. 16/025,568, entitled MEDICAL PRODUCT AND METHOD FOR ELIMINATING SYMPTOMS OF NICOTINE WITHDRAWAL, and filed on Jul. 2, 2018, as being generally related to methods of using an active mesh nebulizer, are incorporated herein by reference.

BACKGROUND

Alcohol consumption is a practice undertaken by many for recreational purposes. However, alcohol consumption is associated with an elevated risk of premature death due to, for example, traffic accidents, cancer, and organ damage. Further, fetal alcohol syndrome is a result of alcohol consumption during pregnancy with lifelong impact on the child and no known remedy.

BRIEF DESCRIPTION OF THE DRAWINGS

FIG. 1 is a flow diagram of a method of delivering alcohol to a person that avoids hangover symptoms, according to some embodiments.

DETAILED DESCRIPTION

The following disclosure provides many different embodiments, or examples, for implementing different features of the provided subject matter. Specific examples of components, values, operations, materials, arrangements, etc., are described below to simplify the present disclosure. These are, of course, merely examples and are not intended to be limiting. Other components, values, operations, materials, arrangements, and so forth, are contemplated. In addition, the present disclosure may repeat reference numerals and/or letters in the various examples. This repetition is for the purpose of simplicity and clarity and does not in itself dictate a relationship between the various embodiments and/or configurations discussed. Aspects of the present disclosure are best understood from the following detailed description when read with the accompanying FIGURES.

The use of an active mesh nebulizer with lockout bar coded capsules/cartridges to help aid most consequences of alcohol use syndrome. Capsules coded with a bar code or other identifying mark (e.g., a QR code) or electronic identifier (radio frequency identifier—RFID) is used to regulate access by the nebulizer to a solution to be nebulized. In some embodiments of the nebulizer, a capsule (or, cartridge) containing ethyl alcohol or an ethyl alcohol solution is a single-use capsule. In some embodiments, the capsule or cartridge has a liquid fill volume of at least 0.5 milliliters and not more than 10 milliliters. In some instances, the liquid fill volume of a capsule or cartridge ranges from at least 1 ml to not more than 5 ml. In a preferred embodiment, the capsule has a liquid fill volume of about 4 ml. A fill volume greater than about 10 ml is inconvenient to carry because of the size of the capsule, and a difficulty of extracting liquid from the capsule after more than 70% of the fluid located therein has been volatilized. At liquid fill volumes less than 0.5 ml, the surface tension of the fluid in the capsule draws a majority of the fluid against the metal mesh that volatilizes the liquid, making regulation of fluid level difficult to manage. Thus, a minor child or a person who does not own a nebulizer is restricted from using the nebulizer against a predetermined usage plan. A lock out barcoded capsule containing ethyl alcohol, tethered to a smartphone application that regulates operation of an active mesh nebulizer, prevents unauthorized use by non-designated users of the active mesh nebulizer, and/or excessive use, misuse, or abuse by a designated user.

Annually in the United States, approximately 88,000 deaths are associated with consequences of alcohol consumption. According to the National Institute of Health (NIH) 2016 statistics, excluding traffic deaths of approximately 10,000 persons, 62,000 men and 26,000 women die from alcohol-related conditions. Liver deaths affect approximately 21,815 persons. Other alcohol-related deaths affect about 34,865 persons, including cancer deaths associated with alcohol use include mouth, tongue, esophagus, pancreas, stomach, colon and breast. Fetal alcohol syndrome is found in 1/100 births or about 44,000 annually. Fetal alcohol syndrome is life long and has no known antidote as of 2018.

According to present theory and belief, delivery of volatilized ethyl alcohol (pure, or in a solution) to the brain via nebulized (as described hereinbelow) particles absorbed through the alveoli produces a brain effect ("buzz" or "intoxication") within 60 seconds without production of alcohol-related metabolites that induce hangover symptoms (also called "body effects", which may include some brain-related symptoms). In some embodiments, delivery of ethyl alcohol produces onset of a brain effect within 10 seconds. In some embodiments, cessation of a brain effect occurs rapidly, with no protracted or elongated recovery period (e.g. a recovery period in which residual ethyl alcohol in a person causes decreased coordination or cognition, while the euphoric portion of a brain effect has ceased).

Ethyl alcohol is an amphiphilic molecule, with a hydrophilic portion (the hydroxyl (—OH) functional group) and a hydrophobic portion) the ethyl (—$C_2H_5$) moiety. The brain is known to have a large proportion of fat or aliphatic molecules located therein. Ethyl alcohol rapidly printed traits the brain blood barrier such that brain tissue rapidly absorbs ethyl alcohol from the bloodstream.

Ethyl alcohol is added to the bloodstream by using an active mesh nebulizer to generate small particles of ethyl alcohol solution in a stream of air inhaled into the lungs during respiration. As described hereinabove by reference, small particles of ethyl alcohol solution produced by an active mesh nebulizer have a size between 0.5 and 5 micrometers (μm) in diameter. Small particles having a size between 0.5 and 5 μm enter alveoli in the lungs rapidly, and have a high residence time within the alveoli before being absorbed into the bloodstream.

Particles with a diameter greater than 10 μm adhere to tissues in the nose and throat. Particles with a diameter smaller than 10 μm are inhalable (enter the lungs) without being trapped on surfaces or tissues in the nose and throat. Particles with diameters smaller than about 5 μm are respirable, or able to penetrate deep into the lungs. Thus, droplets of alcohol solution having a diameter ranging between 0.5 and 5 μm are able to penetrate deep into the lungs, and coat inner surfaces of the tracheobronchial regions. Because alveoli contain thin membranes through which gasses are exchanged between the blood and air within the lungs, particles or liquid droplets which enter alveoli have an effect on respiration rates and health. Ethyl alcohol solution droplets in the alveoli are readily absorbed by the blood by directly crossing the alveoli membrane.

Venous blood from the body and brain enters the right atrium of the heart. The right atrium pumps venous blood into the right ventricle, from which the venous blood is pumped into the lungs for oxygenation. Oxygenated blood received from the lungs enters the left atrium of the heart. The left atrium pumps oxygenated blood into the left ventricle, from which oxygenated blood is pumped out of the heart and to the body. Alcohol absorbed directly into the blood from alveoli of the lungs passes through the left atrium and the left ventricle before flowing to the remainder of the body.

Approximately 20% of the blood flowing from the heart is pumped directly to the brain. Blood exiting the heart from left ventricle returns to the heart within about one minute. Thus, approximately 20% of alcohol directly absorbed into the blood from the lungs travels to the brain within 60 seconds of uptake in the lungs.

Because ethyl alcohol has a lipophilic (or, hydrophobic) ethyl moiety, ethyl alcohol is readily taken up by fat in brain tissue. Thus, delivery of nebulized ethyl alcohol using an active mesh nebulizer as described hereinabove by reference produces a brain effect, whether a "buzz" or intoxication, for small volumes of alcohol solution being nebulized.

FIG. 1 is a flow diagram of a method 100 of delivering ethyl alcohol during respiration without significant body effects, according to an embodiment. In an operation 105, a nebulizer has a control system that is evaluated to determine whether an operational limit of the nebulizer has been exceeded. And operational limits of an active mesh nebulizer includes one or more of a measured volume of delivered alcohol solution, an elapsed time between delivery sessions of alcohol from the active mesh nebulizer, a calculated blood-alcohol content of a nebulizer user, a match between an identifier associated with a capsule or cartridge fitted onto an active mesh nebulizer at the start of an operational period, and an identifier associated with the capsule or cartridge at a later time when a nebulizer airstream is requested, and/or an elapsed time over which a predetermined volume of alcohol solution has been delivered by the active mesh nebulizer.

From operation 105, when an operation limit has not been exceeded, the method continues with operation 110. From operation 105, when an operation limit is exceeded, the method continues with operation 140.

In operation 110, a surface of an ethyl alcohol solution is positioned in contact with an active mesh of a nebulizer, according to some embodiments. As described herein, and active mesh nebulizer includes a vibrating metal mesh withholds situated therein. When a solution service is in contact with the vibrating metal mesh, and the vibrating metal mesh is activated to vibrate at high velocity, droplets of solution are generated above the metal mesh. A quantity of droplets of solution is regulated by controlling a duration of metal mesh vibration. A greater quantity of droplets is provided by the active mesh nebulizer with a longer vibration time, according to either a predetermined vibration time programmed into the active mesh nebulizer, or according to a user requested vibration time.

In an operation 115, the active mesh nebulizer performs a cleaning step, in which the vibrating mesh vibrates while not in contact with a solution situated in a capsule attached to the active mesh nebulizer. Operation 115 is an optional operation. In some embodiments, operation 115 occurs after an elapsed time after capsule placement within the active mesh nebulizer has occurred in order to reduce a quantity of contaminants in a stream of particles generated by the active mesh nebulizer. Particles include, in some embodiments, portions of biofilm or bacterial contamination present within the active mesh nebulizer. Bacterial contamination or biofilm forms within a nebulizer as a function of suitable growing conditions within a favorable range of temperature and humidity for growth of contaminating organisms. A lock-out bar-coded capsule reduces growth of bacterial contamination and biofilms by preventing cross-contamination of a nebulizer from multiple capsules.

In an operation 120, an active mesh nebulizer determines whether or not inhalation is occurring. When inhalation occurs, the method continues with operation 125. When inhalation is not occurring, method 100 continues with operation 122 wherein the nebulizer performs a wait operation. Operation 122 has a duration that is preprogrammed into the nebulizer, or is modified by a user, according to some embodiments. For example, in a non-limiting embodiment of the method, operation 122 continues for 0.5 seconds, after which method 100 continues to operation 120. Upper time for wait time (5 or 10 seconds).

In operation 125, an active mesh nebulizer performs a volatilization step, in which the vibrating mesh begins high-frequency motion against a surface of the solution located in the nebulizer capsule to generate a stream of particles. In operation 130, the stream of particles is added to a flow of air during the inhalation process. According to some embodiments, operation 125 occurs before operation 120. In a preferred embodiment, operation 125 occurs after operation 120 has been performed. In operation 135, the volatilization process ends as the metal mesh vibration is halted. From operation 135, method 100 continues to operation 105, wherein the nebulizer determines whether an operation limit of the nebulizer has been exceeded.

In operation 140, nebulizer operation halts. Method 100 proceeds from operation 105 to operation 140 when a sufficient quantity of particles has been delivered (e.g., the operation limit of sufficient particle quantity has been exceeded).

In some embodiments, a minor brain effect, or buzz, is generated by nebulization and delivery of 2 milliliters (mL) of ethyl alcohol solution having 40% of ethyl alcohol and 60% water. In some embodiments, a major brain effect, or intoxication, is generated by nebulization of 2 mL of ethyl alcohol solution having 60% ethyl alcohol and 40% water. An active mesh nebulizer is configured to nebulize an ethyl alcohol-containing solution ranging from about 1% up to 100% ethyl alcohol. It is noted, however, that the degree a brain effect of ethyl alcohol solution delivered by nebulization is affected by body mass of an individual, gender of the individual, personal tolerance of alcohol delivery, and body composition of the individual, among other factors. Thus, individual brain effects resulting from delivery of nebulae stuff alcohol solutions using an active mesh nebulizer as described hereinabove are highly variable, but the general principle of rapid occurrence of a brain effect caused by nebulization should be understood to be a result of the particle size of ethyl alcohol solution droplets generated by the active mesh nebulizer and the rapid uptake of ethyl alcohol by blood solution in the lungs after respiration of said particles.

A relevant feature of delivery of ethyl alcohol solution particles to the lung by an active mesh nebulizer is that the brain affect caused by the absorbed of alcohol has a rapid onset, but is not followed by deleterious effects of intoxication when the brain effect ceases. The small volume of alcohol solution delivered to the bloodstream through the lungs by the active mesh nebulizer induces rapid brain affect because a significant portion (approximately 20%) of the absorbed alcohol travels directly to the brain. The remaining volume of alcohol not delivered directly to the brain (approximately 80%) circulates the remainder of the body. Some or all of the remaining volume of alcohol is absorbed by other body tissues, including the liver. An amount of alcohol dehydrogenase located in the liver is sufficient to receive and metabolize alcohol received an absorbed by the liver, producing known and recognized alcohol metabolic byproducts, including acetaldehyde. It is of note, however, that the amount of acetaldehyde and other alcohol metabolic byproducts, is greatly reduced with respect to traditional alcohol consumption techniques, drinking and absorption of the alcohol through the stomach and small intestine.

The onset of brain effect after delivery of volatilized ethyl alcohol solution occurs within 60 seconds. In some embodiments, the onset of brain effect occurs within 10 seconds of the initial delivery of volatilized ethyl alcohol. Onset of a brain effect occurs after volatilization (or, nebulization) of less than 0.5 ml ethyl alcohol solution. Thus, a quantity of ethyl alcohol in the blood is below a detection threshold of a blood alcohol content (BAC) blood test, or a test that monitors alcohol vapor upon breathing through a test apparatus (e.g., a "breathalyzer" test).

Ethyl alcohol produces a brain effect by disrupting neurotransmitter production. Brain effects from ethyl alcohol continue for approximately as long as a concentration of ethyl alcohol in the brain exceeds an intoxication threshold. Once a concentration of ethyl alcohol in the brain falls below the intoxication threshold, the neurotransmitter disrupting effects of ethyl alcohol cease and the brain effect is no longer experienced. Thus, according to current theory and belief, cessation of a brain effect of ethyl alcohol occurs rapidly (e.g., within less than about 10 minutes from an "effected" state as the brain tissues metabolizes ethyl alcohol absorbed by brain tissue. Because there is no "reservoir" of unabsorbed or unmetabolized alcohol in the stomach, intestine, blood, or other body tissues, the brain effect of alcohol ceases rapidly, as described above. Thus, after an abbreviated recovery period following cessation of brain effect subsequent to delivery of alcohol to brain tissue using an active mesh nebulizer, there is no residual mental incapacitation or adverse effect on cognitive ability. In some embodiments, rapid cessation of brain effect includes rapid return of physical coordination and/or motor skills. Thus, when a subject has received an ethyl alcohol delivery by means of an active mesh nebulizer as described hereinabove, upon cessation of the euphoric brain effect and the abbreviated recovery period, there is no residual deleterious cognitive effect or adverse impact on coordination or motor skills. Rather, a subject returns to a fully sober state extremely rapidly. According to theory and belief, the abbreviated recovery period for a return to full sobriety is not less than around 1 minute, and not greater than about 20 minutes, according to an amount of delivered ethyl alcohol. In some embodiments, the recovery period for a return to full sobriety subsequent to cessation of euphoric brain effect is between about 5 and about 10 minutes. Thus a subject, having received a delivery of nebulized (or volatilized) ethyl alcohol as described herein by an active mesh nebulizer, is able to, e.g., operate a motor vehicle or perform cognitively demanding operations in a manner consistent with the subject's pre-delivery capacity immediately after the recovery period after cessation of the euphoric brain effect. When the cessation of brain effect occurs, in some instances the recovery period is immediate (less than one minute). When the brain effect ends, because there is such a small amount of alcohol present in the brain and body of a person to whom the alcohol has been delivered, the common physical consequences of intoxication or drunkenness are less likely to occur. Consequences such as dizziness, falling, automobile accidents, and so forth are reduced and/or eliminated because the balance and coordination of a person with alcohol in the brain is impacted by the brain alcohol content. When the alcohol content in the brain drops below a threshold level, the physical coordination and balance return rapidly and the consequences of falling (sprains, bone breakage, concussion, torn muscle or ligament/tendon) are reduced or eliminated because the person is readily aware of the return of sobriety and mental clarity to the person.

Some aspects of the present disclosure relate to a method of delivering alcohol to a person with a brain effect (euphoria, and so forth) with a blood alcohol limit that is less than 0.02% and more than 0.0001%.

While the brain affect caused by nebulization of ethyl alcohol solutions occurs quickly, and with relatively small volume of nebulized ethyl alcohol solutions, body effects of alcohol consumption are reduced and/or eliminated. Short-term body effects include "hangover" symptoms, such as fatigue, weakness, excessive thirst, headaches, muscle aches, nausea, and vomiting. Other "hangover" symptoms include dizziness, sleep disruption, sensitivity to light and sound, and shakiness. Long-term body effects of alcohol consumption include damage to the gastrointestinal tract, liver cirrhosis, heart damage, elevated triglyceride levels, fat buildup in the liver, and pancreatitis. Long-term body effects of alcohol consumption also include elevated cancer risks as described above. Further, fetal alcohol syndrome is associated with alcohol consumption during pregnancy with life-long effects on cognitive function and physical coordination of the child.

According to present theory and understanding, delivery of alcohol by means of an active mesh nebulizer produces rapid brain affect and little or no short term body affects. In some instances, delivery of alcohol using an active message nebulizer produces mild and or pronounced brain effects with no "hangover" symptoms when the brain effective alcohol delivery ends.

As described previously, active mesh nebulizers neither heat nor boil liquids located therein. Rather, active mesh nebulizers contain a metallic grid with numerous small diameter holes located therein. The metallic grid is placed in contact with liquid within the nebulizer, after which the grid is rapidly vibrated to generate particles and liquid with diameters as described hereinabove. Some embodiments of active mesh nebulizers include grids containing thousands of perforations or holes, wherein said grids are made of piezoelectric materials that oscillate upon electrical stimulation.

One feature of active mesh nebulizers is that metallic grid self cleans upon vibration of the grid. Particles, liquids, or films coding the grid are vibrated off of a metallic grid surface when the grid is vibrated for extended periods (e.g., vibrational periods lasting three seconds or longer). Thus, each operation of a metallic grid to generate droplets of solution can include, according to some embodiments, an initial cleaning phase, and a droplet formation phase after the cleaning phase. By dividing metallic grid operation into two phases, the stream of particles generated by the active mesh nebulizer to be delivered into the lung for uptake by the blood has a reduced incidence of bacterial or other contaminants, as compared to nebulizers that generate droplets using methods other than vibrating metallic grids.

According to present theory and understanding, delivery of alcohol by means of an active mesh nebulizer provides a user an opportunity to consume alcohol with brain effect and also provide other body tissues, including heart, gastrointestinal tract, liver, bladder, and so forth, opportunity to heal from previously incurred tissue damage caused by alcohol consumption. For example, a patient in a rehabilitation facility is able to receive delivered alcohol in quantities configured to achieve brain effect during addiction treatment without incurring additional tissue damage. Thus, symptoms of alcohol withdrawal are minimized during a alcohol addiction treatment process, without incurring further gross bodily damage associated with large quantities of alcohol commonly associated with drinking. For example, symptoms of alcohol withdrawal include (for mild severity): anxiety, insomnia, nausea, and abdominal pain; (for moderate severity) elevated blood pressure, elevated body temperature, heart rate variation, mental confusion; and (for high severity) hallucinations, fever, seizures (delerium tremors), and/or agitation. Alcohol delivery via the lungs and absorption through the blood to moderate withdrawal symptoms occurs for periods up to 10 days in order to regulate withdrawal symptoms without inducing additional addictive behaviors or additional tissue damage by a patient undergoing withdrawal therapy and assistance. Timing and dosage of alcohol delivery using volatilized droplets, as described hereinabove, are determined according to a patient response to alcohol delivery, a patient tolerance to alcohol, and severity and type of symptoms experienced by a patient.

According to present theory and understanding, a person without any alcohol-related tissue damage (e.g., in the gastro-intestinal tract, liver, or cancer symptoms) experiences delivery of alcohol to the brain by means of an active mesh nebulizer to achieve a euphoric brain effect with no, or only minor, tissue damage or alcohol toxicity-related symptoms associated with consumption of large amounts of alcohol. The benefit to a user is that euphoric effects are experienced with little, or no, gross tissue damage or increased cancer risk associated with alcohol consumption.

A further aspect of the present disclosure is an increased degree of accuracy in alcohol delivery to a user, or accurately titrate the central nervous system. Because an active mesh nebulizer is capable of quantifying an amount of alcohol solution delivered to a use (by, for example, monitoring a time period during which the active mesh vibrates to generate a particle stream, and/or by monitoring a remaining level of alcohol solution within the nebulizer), the user is able to monitor and regulate alcohol consumption with greater precision than by drinking alcohol. Further, some embodiments of an active mesh nebulizer are programmed to deliver a predetermined amount of alcohol to a user before halting further delivery to allow a user to recover from the brain affect before further delivery of nebulized particles occurs.

The use of this nebulizer will allow the individual to accurately titrate their central nervous system effect as previously described. Some embodiments of an active mesh nebulizer are configured to adjust generation and delivery of nebulized ethyl alcohol solution to a user by pre-programming the active mesh nebulizer with a set of user parameters. These parameters include, in some embodiments, body mass, gender, body composition, desired level of brain effect (determined empirically and provided by a user), and so forth. Some embodiments of active mesh nebulizers include a performance lockout system figured to recognize a concentration of ethyl alcohol in a solution contained in a nebulizer capsule. Some embodiments of active mesh nebulizers include a performance lockout system that halts further droplet production when a nebulizer capsule is removed from the nebulizer and a new nebulizer capsule is added to the nebulizer. Nebulizer capsules include, in some embodiments, barcodes or other identification means configured to provide a nebulizer with capsule content information.

Long-term body effects of alcohol consumption, including effects on peripheral nerves, the liver, and gastrointestinal tract, are largely dependent on the dose, or quantity of alcohol consumed by an individual. The higher the concentration of alcohol in the blood, or blood-alcohol content, and the longer period of time alcohol is consumed, the greater the damage that is likely to occur to an individual. Despite individual variations regarding tolerance of alcohol exposure, where some individuals experience harm and some do not at the same level of acute or chronic exposure, tissue damage generally follows long term exposure and high levels of exposure to ingested alcohol. Alcohol delivery through the lung by means of small (0.5-5 micrometer) droplets reduces the overall exposure of body tissues to ethyl alcohol while providing similar (e.g., euphoric) brain effects with greatly reduced risk of developing illness or tissue damage associated with long-term alcohol exposure. There is no known dose/consequence relationship.

This application describes the use of an active mesh nebulizer which produces very small particles (1-5 micron) of ethyl alcohol in various concentrations to produce an easily titrated effect and avoid damage to the liver, gastrointestinal tract or peripheral nervous system. This effect is short lived (30 minutes to 2 or more hours) and allows tissues already damaged by alcohol abuse to heal. It also avoids central nervous system alcohol withdrawal and could be useful to treat hangovers in some individuals. A single use lock out barcoded capsule/cartridge containing ethyl alcohol in various concentrations along with a tethered smartphone application prevents unauthorized use by others as well.

Alcohol is a very small molecule which has the unusual property of being both hydrophilic and lipophilic. Alcohol enters the brain by two pathways. First, Filtration which allows alcohol to move through the water spaces because it dissolves in water. Second, passive diffusion due to the lipophilic nature of ethanol. This allows it to move without transport molecules across cell membranes and into the brain.

Other small lipophilic molecules can also move passively across the blood brain barrier. These include nicotine, marijuana, heroin, fentanyl, and other opioids, all have a significant brain effects. Glucose and vitamins are carried across the blood brain barrier by transport molecules and this process is known as active transportation and requires energy expenditure not seen with lipophilic compounds such as alcohol.

Ingested alcohol is metabolized in the liver by alcohol dehydrogenase to produce acetaldehyde which is the molecule that causes nausea, headache, fatigue and other toxic side effects recognized in the hangover syndrome.

Our device which uses much smaller amounts of ethanol and bypasses the liver largely avoids the toxic side effects of acetaldehyde as only very small amounts of alcohol dehydrogenase would be needed to eliminate it from the brain. Additionally, acetaldehyde has been implicated as the responsible agent in the relationship between alcohol consumption and increased cancer risk.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method, comprising:
   volatilizing a liquid containing ethyl alcohol using an active mesh nebulizer to produce a stream of ethyl alcohol particles;
   delivering the stream of volatilized ethyl alcohol particles into a flow of gas during inhalation; wherein, upon completing delivering the stream of volatilized ethyl alcohol particles, a blood alcohol content greater than 0.0001% and less than 0.02% is achieved.

2. The method of claim 1, further comprising monitoring a quantity of volatilized ethyl alcohol particles delivered during inhalation.

3. The method of claim 1, further comprising producing a brain effect within less than 60 seconds subsequent to delivering the stream of volatilized ethyl alcohol particles during inhalation.

4. The method of claim 1, further comprising halting the stream of ethyl alcohol particles upon exceeding an operation limit of the active mesh nebulizer.

5. The method of claim 1, further comprising monitoring a period of time between an initial delivery of particles and a current time, and allowing delivery of particles based on an elapsed time between the current time and the initial delivery of particles.

6. The method of claim 1, wherein delivering the stream of volatilized ethyl alcohol particles produces a brain effect with a blood alcohol content below a level which produces side effects to the liver, peripheral nervous system and gastrointestinal tract.

7. The method of claim 1, wherein delivering the stream of volatilized ethyl alcohol particles produces a brain effect with a blood alcohol content below a level which produces hangover symptoms.

8. A method, comprising providing a quantity of ethyl alcohol particles having diameters less than 5 micrometers to persons experiencing alcohol withdrawal symptoms to mitigate alcohol withdrawal symptoms, wherein, upon providing the quantity of ethyl alcohol particles, blood alcohol is greater than 0.0001% and less than 0.02%.

9. The method of claim 8, wherein providing a quantity of ethyl alcohol particles to mitigate alcohol withdrawal symptoms further comprises mitigating hallucinations, seizures, and/or delirium tremens.

10. The method of claim 8, wherein providing the quantity of ethyl alcohol particles to persons experiencing alcohol withdrawal symptoms minimizes gastrointestinal damage, liver damage, or peripheral nervous system damage while satisfying a user desire for euphoric brain effect.

11. The method of claim 10, wherein cessation of a brain effect caused by ethyl alcohol occurs within 5 minutes.

12. The method of claim 11, wherein, immediately after a recovery period following cessation of a brain effect caused by ethyl alcohol, no adverse effect on motor skills or cognitive ability occurs.

13. The method of claim 12, wherein, after cessation of the brain effect caused by ethyl alcohol, a person having received delivered ethyl alcohol can operate a motor vehicle with no motor impairment and no detectable blood alcohol content.

* * * * *